United States Patent
Ward et al.

(10) Patent No.: US 9,757,185 B2
(45) Date of Patent: Sep. 12, 2017

(54) QUADRIPOLAR FORCEPS

(71) Applicant: Gyrus ACMI, Inc., Southborough, MA (US)

(72) Inventors: Zane R. Ward, Prior Lake, MN (US); Richard J. Curtis, Maple Grove, MN (US)

(73) Assignee: Gyrus ACMI, Inc., Southborough, MA (US)

( * ) Notice: Subject to any disclaimer, the term of this patent is extended or adjusted under 35 U.S.C. 154(b) by 415 days.

(21) Appl. No.: 14/087,474

(22) Filed: Nov. 22, 2013

(65) Prior Publication Data

US 2014/0148804 A1    May 29, 2014

Related U.S. Application Data

(60) Provisional application No. 61/731,195, filed on Nov. 29, 2012.

(51) Int. Cl.
| | |
|---|---|
| *A61B 18/18* | (2006.01) |
| *A61B 18/14* | (2006.01) |
| *A61B 18/12* | (2006.01) |

(52) U.S. Cl.
CPC ...... *A61B 18/1442* (2013.01); *A61B 18/1206* (2013.01); *A61B 18/1445* (2013.01);
(Continued)

(58) Field of Classification Search
CPC ............ A61B 18/1206; A61B 18/1442; A61B 18/1445; A61B 2018/124; A61B 2018/126; A61B 2018/1273; A61B 2018/1286
(Continued)

(56) References Cited

U.S. PATENT DOCUMENTS

| | | |
|---|---|---|
| 3,683,923 A | 8/1972 | Anderson |
| 4,532,924 A | 8/1985 | Auth et al. |

(Continued)

FOREIGN PATENT DOCUMENTS

| | | |
|---|---|---|
| EP | 0832612 A1 | 1/1998 |
| EP | 1795140 A1 | 6/2007 |

(Continued)

OTHER PUBLICATIONS

International Search Report PCT/US2013/071706.
Everest Medical QUADripolar(TM) Cutting Forceps. Marketing Material, Everest Medical Laboratory, Edison, NJ.

*Primary Examiner* — Michael Peffley
*Assistant Examiner* — Amanda Zink
(74) *Attorney, Agent, or Firm* — Chapin IP Law, LLC

(57) ABSTRACT

Electrosurgical forceps that can provide improved hemostatis and tissue-cutting capabilities during surgical procedures. The electrosurgical forceps include opposing jaw members, each including first and second electrode members. The first and second electrodes included in the respective jaw members are disposed directly opposite one another, the first electrode members included in the respective jaw members are disposed diagonally opposite one another, and the second electrode members included in the respective jaw members are disposed diagonally opposite one another. A first high frequency (HF) electric power source is connectable across the first electrode members, and a second HF electric power source is connectable across the second electrode members, electrically isolating the first electrode members from the second electrode members, and allowing current to flow diagonally through the tissue between one or both of the first electrode members and the second electrode members.

9 Claims, 7 Drawing Sheets

(52) U.S. Cl.
CPC ... *A61B 2018/124* (2013.01); *A61B 2018/126* (2013.01); *A61B 2018/1273* (2013.01); *A61B 2018/1286* (2013.01)

(58) Field of Classification Search
USPC ..................................................... 606/32–52
See application file for complete search history.

(56) References Cited

U.S. PATENT DOCUMENTS

| | | | |
|---|---|---|---|
| 4,938,761 A | 7/1990 | Ensslin | |
| 5,318,564 A | 6/1994 | Eggers | |
| 5,443,463 A * | 8/1995 | Stern | A61N 1/40 606/51 |
| 5,480,399 A | 1/1996 | Hebborn | |
| 5,540,682 A | 7/1996 | Adelinia et al. | |
| 5,810,811 A | 9/1998 | Yates | |
| 5,833,690 A | 11/1998 | Yates et al. | |
| 5,919,189 A * | 7/1999 | Benderev | A61B 18/149 606/41 |
| 5,931,836 A | 8/1999 | Gotanda et al. | |
| 6,030,384 A | 2/2000 | Nezhat | |
| 6,086,586 A | 7/2000 | Hooven | |
| 6,113,596 A | 9/2000 | Hooven et al. | |
| 6,152,923 A * | 11/2000 | Ryan | A61B 18/1445 606/42 |
| 6,926,716 B2 | 8/2005 | Baker et al. | |
| 7,041,102 B2 | 5/2006 | Truckai | |
| 7,153,300 B2 * | 12/2006 | Goble | A61B 18/1206 606/37 |
| 7,160,298 B2 | 1/2007 | Lawes | |
| 7,160,299 B2 | 1/2007 | Baily | |
| 7,276,068 B2 | 10/2007 | Johnson et al. | |
| 7,344,532 B2 * | 3/2008 | Goble | A61B 18/1206 606/34 |
| 7,604,635 B2 | 10/2009 | McClurken | |
| 7,674,258 B2 | 3/2010 | Swanson | |
| 7,794,461 B2 | 9/2010 | Eder | |
| 7,803,156 B2 | 9/2010 | Eder | |
| 7,862,560 B2 | 1/2011 | Marion | |
| 7,862,565 B2 | 1/2011 | Eder | |
| 7,909,820 B2 | 3/2011 | Lipson et al. | |
| 7,942,874 B2 | 5/2011 | Eder | |
| 8,162,940 B2 | 4/2012 | Johnson | |
| 2003/0139741 A1 | 7/2003 | Goble et al. | |
| 2006/0025765 A1 | 2/2006 | Landman | |
| 2006/0217709 A1 | 9/2006 | Couture et al. | |
| 2007/0299440 A1 | 12/2007 | Mauti | |
| 2008/0071260 A1 | 3/2008 | Shores | |
| 2008/0300590 A1 | 12/2008 | Horne et al. | |
| 2010/0268211 A1 | 10/2010 | Manwaring et al. | |
| 2012/0078139 A1 | 3/2012 | Aldridge et al. | |

FOREIGN PATENT DOCUMENTS

| | | |
|---|---|---|
| EP | 1958583 A2 | 8/2008 |
| EP | 2147649 A1 | 1/2010 |
| GB | 2447767 A | 9/2008 |
| WO | 0059397 A1 | 10/2000 |
| WO | 2004032777 A1 | 4/2004 |

\* cited by examiner

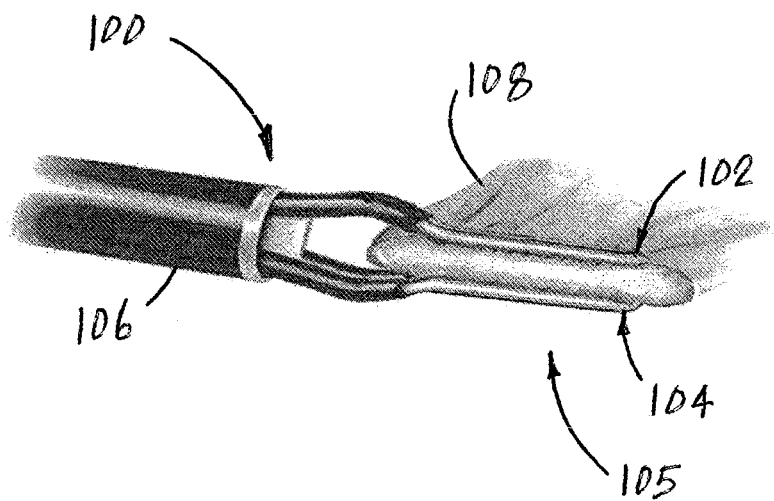
Fig. 1a – Prior art
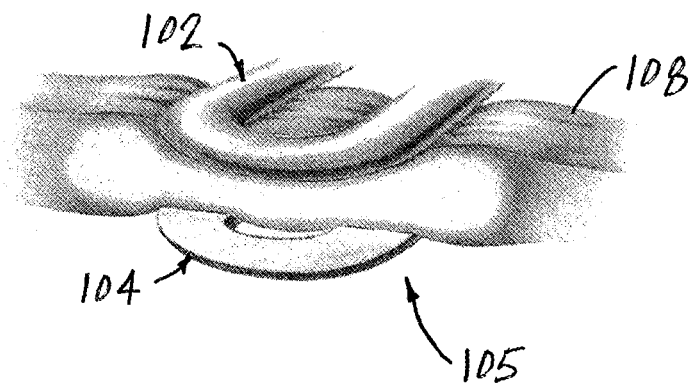
Fig. 1b – Prior art

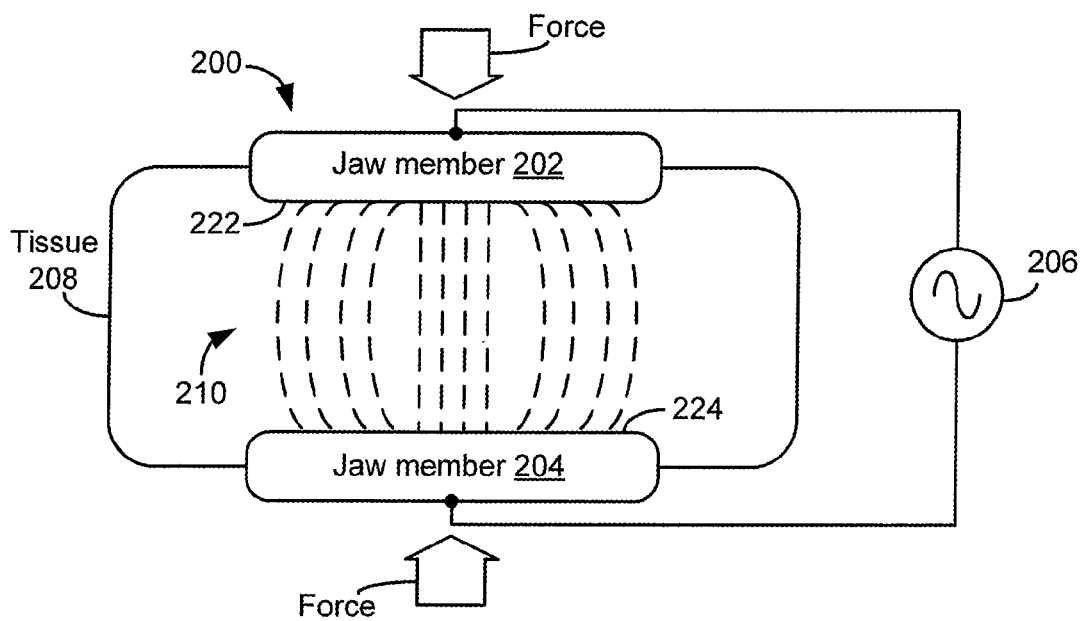
*Fig. 2a – Prior art*
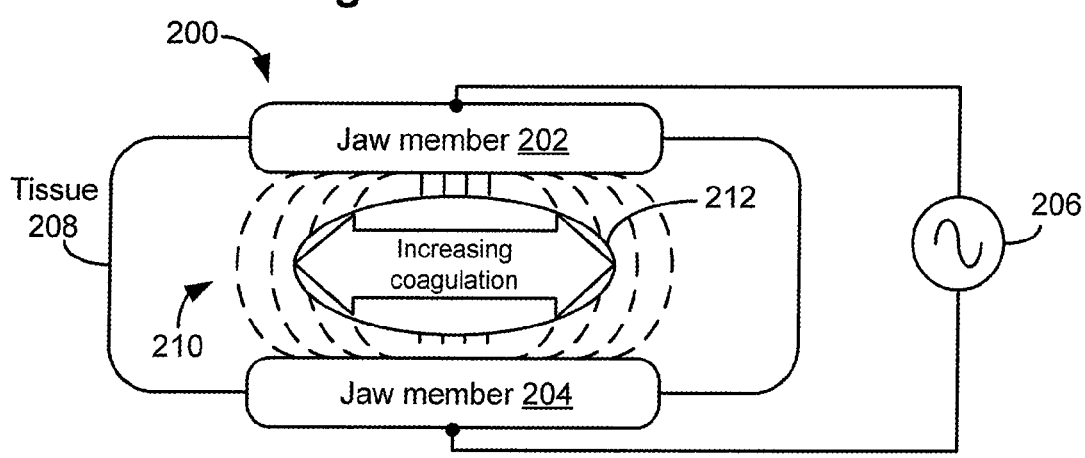
*Fig. 2b – Prior art*
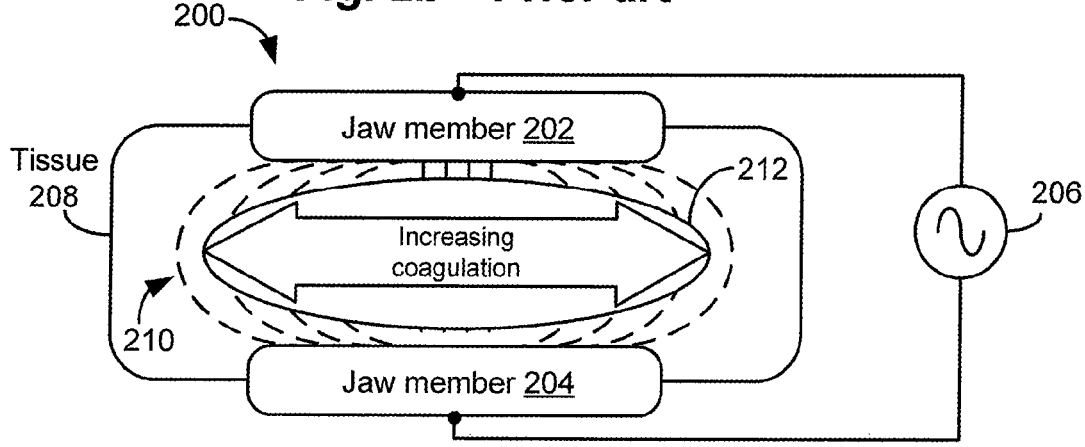
*Fig. 2c – Prior art*

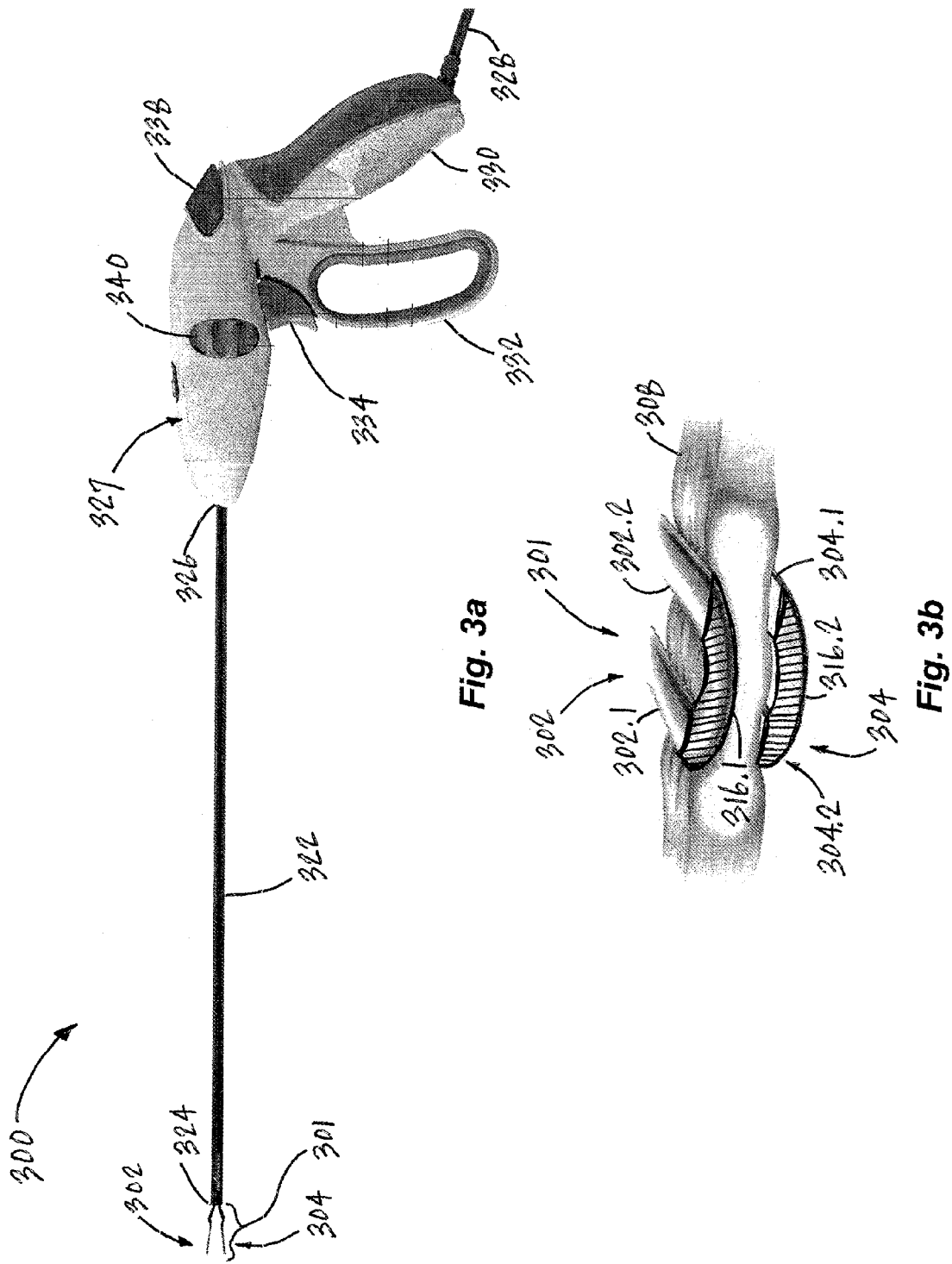

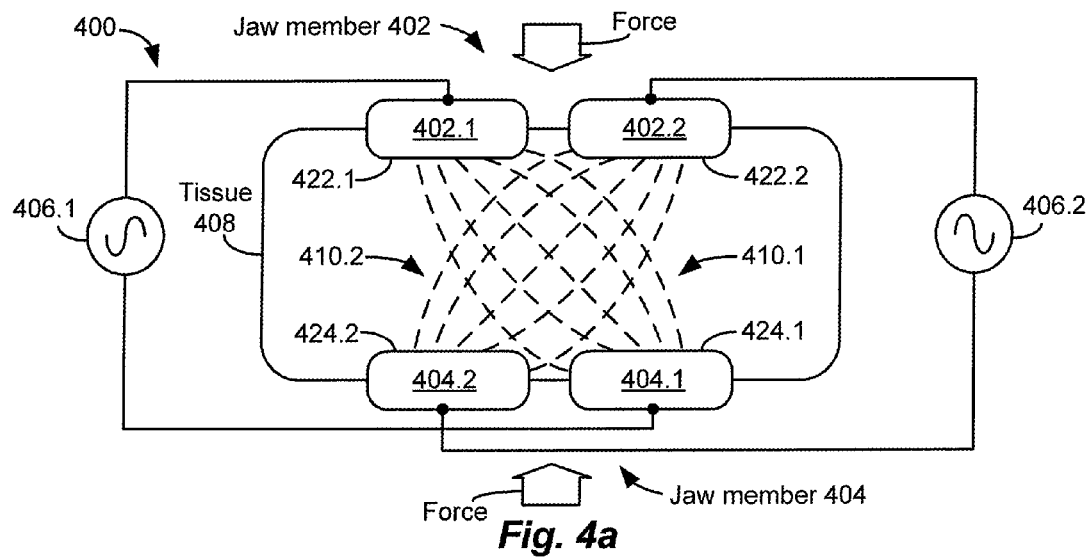
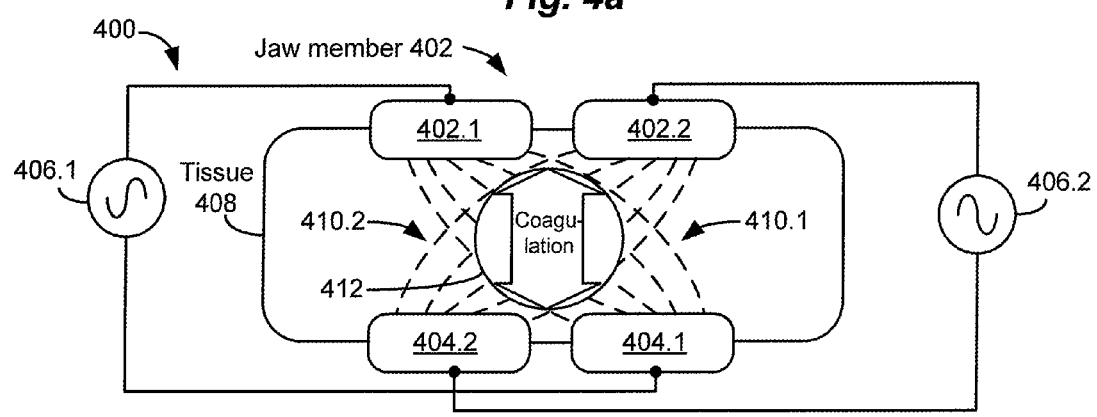
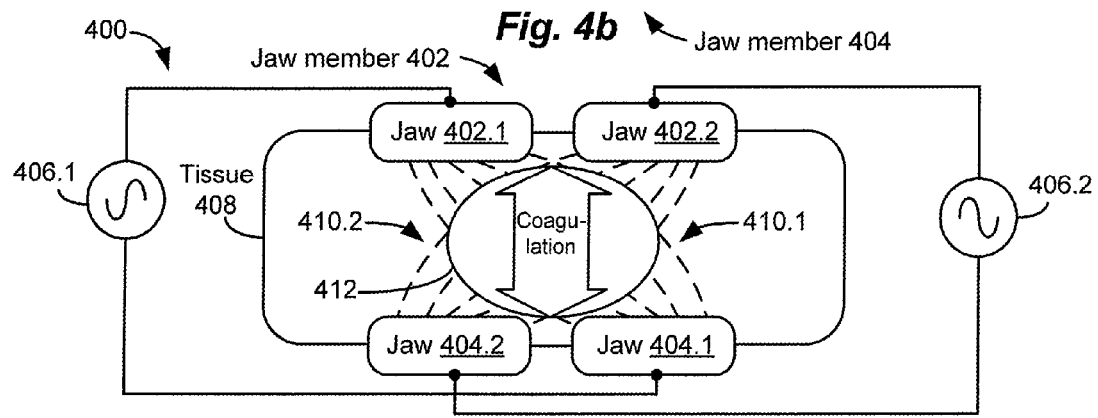

QUADRIPOLAR FORCEPS

CROSS REFERENCE TO RELATED APPLICATIONS

This application claims benefit of the priority of U.S. Provisional Patent Application No. 61/731,195 filed Nov. 29, 2012 entitled QUADRIPOLAR FORCEPS.

TECHNICAL FIELD

The present application relates generally to electrosurgical instruments, and more specifically to electrosurgical forceps that can provide improved hemostatis and tissue-cutting capabilities during surgical procedures.

BACKGROUND

Electrosurgical forceps are known that employ mechanical clamping action and electrical energy to cut, cauterize, coagulate, desiccate, and/or reduce bleeding in living tissue during surgical procedures. Conventional electrosurgical forceps typically have a pair of opposing jaw members, each forming an electrode charged to a different electrical potential. The pair of opposing jaw members are configured to grasp the living tissue, and to transfer bipolar energy through the living tissue, allowing a surgeon to effect hemostatis and/or tissue-cutting actions at least in part by controlling the intensity, frequency, and/or duration of the bipolar energy applied between the respective electrodes and through the tissue.

In a typical mode of operation of such conventional electrosurgical forceps, the transfer of bipolar energy through the living tissue initially causes an electrical current to flow through the tissue generally perpendicular to contact surfaces of the opposing jaw members. The flow of electrical current causes the living tissue to coagulate, which, in turn, causes the impedance of the tissue to rise in the region between the contact surfaces of the opposing jaw members. Because uncoagulated tissue in the region generally between the periphery of the respective contact surfaces has a lower impedance compared to the coagulated tissue, the uncoagulated tissue provides a more favorable path for the electrical current to continue flowing through the tissue. As a result, the living tissue between the periphery of the opposing contact surfaces now starts to coagulate, causing what is referred to herein as a "thermal margin" to spread laterally and extend into the tissue beyond the region between the respective jaw members.

The conventional electrosurgical forceps described above have several drawbacks. For example, the thermal margin resulting from use of such conventional electrosurgical forceps can cause the impedance of the tissue near or touching the contact surfaces of the opposing jaw members to increase to a level where the flow of electrical current through the tissue is significantly reduced, possibly preventing further coagulation of the tissue. Moreover, as the thermal margin spreads laterally and extends into the living tissue, tissue structures adjacent the region between the opposing jaw members may potentially become damaged, thereby limiting the overall utility of the conventional electrosurgical forceps.

In addition, because the electrodes formed by the opposing jaw members of such conventional electrosurgical forceps are charged to different electrical potentials, an electrical short circuit can result if the contact surfaces of the opposing jaw members inadvertently touch one another during use. This can sometimes occur if the opposing jaw members grasp very thin tissue, or clamp onto the living tissue with excessive force. Such electrical shorting of the opposing contact surfaces can stop any electrical current from flowing through the living tissue, possibly preventing the conventional electrosurgical forceps from providing hemostatis at a time when it may be most needed.

It would therefore be desirable to have electrosurgical forceps that avoid at least some of the drawbacks of the conventional electrosurgical forceps described above.

SUMMARY

In accordance with the present application, electrosurgical forceps are disclosed that can provide improved hemostatis and tissue-cutting capabilities during surgical procedures. In one aspect, the disclosed electrosurgical forceps include a pair of opposing jaw members configured to grasp living tissue. The pair of opposing jaw members form what is referred to herein as a "quadripolar" electrode assembly, in which each jaw member includes two electrode members, namely, a first electrode member and a second electrode member. The electrode members are configured and arranged within the quadripolar electrode assembly such that the first and second electrodes included in the respective jaw members are disposed directly opposite one another, the first electrode members included in the respective jaw members are disposed diagonally opposite one another, and the second electrode members included in the respective jaw members are likewise disposed diagonally opposite one another. Moreover, a first high frequency (HF) electric power source can be connected across the diagonally opposing first electrode members, and a second HF electric power source can be connected across the diagonally opposing second electrode members, electrically isolating the first electrode members from the second electrode members.

In an exemplary mode of operation, the disclosed electrosurgical forceps are operative to move the pair of opposing jaw members from an open position to a closed position for grasping the living tissue therebetween. The first HF electric power source connected across the first electrode members of the quadripolar electrode assembly can be selectively activated to direct bipolar energy diagonally through the living tissue between the diagonally opposing first electrode members. Likewise, the second HF electric power source connected across the second electrode members of the quadripolar electrode assembly can be selectively activated to direct bipolar energy diagonally through the living tissue between the diagonally opposing second electrode members. Because the first electrode members are electrically isolated from the second electrode members, the bipolar energy generated by the first and second HF electric power sources can cause two separate and isolated electrical currents to flow through the living tissue, namely, a first electrical current flowing through the tissue between the diagonally opposing first electrode members, and a second electrical current flowing through the tissue between the diagonally opposing second electrode members. Moreover, the arrangement of the electrode members within the quadripolar electrode assembly prohibits electrical current from flowing between the first and second electrode members in the same jaw member, as well as between the first and second electrode members disposed directly opposite one another in the opposing jaw members. As a result, the lateral thermal margin is reduced, and the risk of an electrical short circuit, resulting from contact surfaces of the opposing jaw members inadvertently touching one another during use, is substantially eliminated.

Other features, functions, and aspects of the invention will be evident from the Drawings and/or the Detailed Description of the Invention that follow.

BRIEF DESCRIPTION OF THE DRAWINGS

The invention will be more fully understood with reference to the following Detailed Description of the Invention in conjunction with the drawings of which:

FIG. 1a is a perspective view of conventional electrosurgical forceps;

FIG. 1b is another perspective view of the conventional electrosurgical forceps of FIG. 1a;

FIGS. 2a-2c are schematic diagrams illustrating the operation of the conventional electrosurgical forceps of FIGS. 1a and 1b;

FIG. 3a illustrates exemplary electrosurgical forceps configured in accordance with the present application;

FIG. 3b is a perspective view of opposing jaw members forming an exemplary quadripolar electrode assembly for use with the electrosurgical forceps of FIG. 3a;

FIGS. 4a-4c are schematic diagrams illustrating the operation of the electrosurgical forceps of FIG. 3a, incorporating the quadripolar electrode assembly of FIG. 3b;

DETAILED DESCRIPTION

Figure 5A:
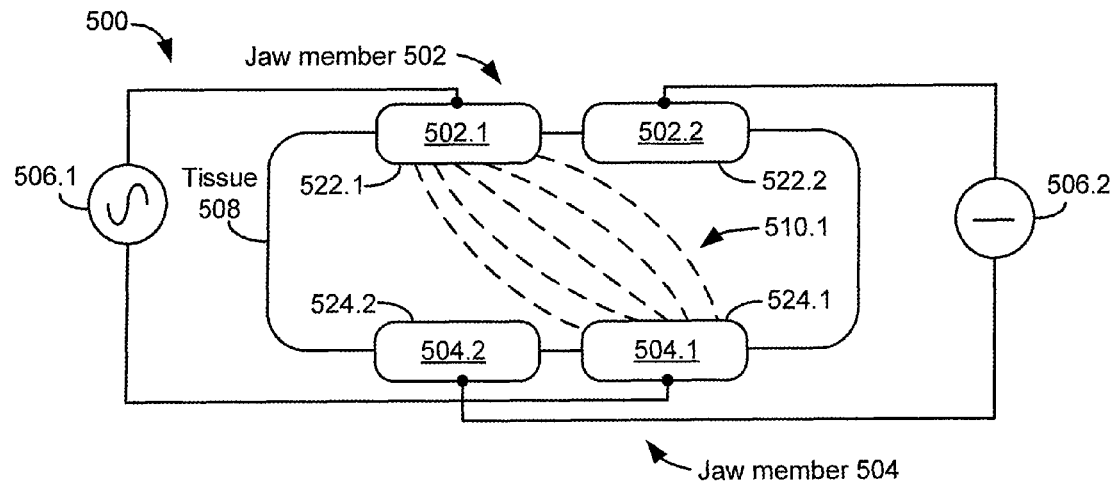
FIGS. 5a and 5b are schematic diagrams further illustrating the operation of the electrosurgical forceps of FIG. 3a, incorporating the quadripolar electrode assembly of FIG. 3b.

The disclosure of U.S. Provisional Patent Application No. 61/731,195 filed Nov. 29, 2012 entitled QUADRIPOLAR FORCEPS is hereby incorporated herein by reference in its entirety.

Electrosurgical forceps are disclosed that can provide improved hemostatis and tissue-cutting capabilities during surgical procedures. The disclosed electrosurgical forceps include a pair of opposing jaw members forming what is referred to herein as a "quadripolar" electrode assembly that can reduce lateral thermal margin through living tissue, and substantially eliminate the risk of an electrical short circuit resulting from contact surfaces of the opposing jaw members inadvertently touching one another during use.

FIG. 1a depicts a partial perspective view of conventional electrosurgical forceps 100. As shown in FIG. 1a, the conventional electrosurgical forceps 100 include a pair of opposing jaw members 102, 104, and a shaft 106. The pair of opposing jaw members 102, 104 are configured to form an electrode assembly 105, and a distal end (not numbered) of the shaft 106 is configured to mechanically engage the electrode assembly 105. A proximal end (not shown) of the shaft 106 is configured to mechanically engage a handle assembly (not shown) of the conventional electrosurgical forceps 100. The handle assembly and the electrode assembly 105 mutually cooperate to move the opposing jaw members 102, 104 from an open position to a closed position (and vice versa) for grasping living tissue 108 therebetween. FIGS. 1a and 1b each depict a partial perspective view of the electrode assembly 105 with the pair of opposing jaw members 102, 104 in the closed position, grasping the living tissue 108. As shown in FIG. 1 b, each of the opposing jaw members 102, 104 forms a single complete electrode member within the electrode assembly 105.

FIGS. 2a-2c are schematic diagrams illustrating the operation of the conventional electrosurgical forceps 100 (see FIGS. 1a and 1b). Specifically, FIGS. 2a-2c depict conventional electrosurgical forceps 200 that include a pair of opposing jaw members 202, 204, which schematically represent the pair of opposing jaw members 102, 104, respectively, included in the conventional electrosurgical forceps 100. As shown in FIG. 2a, in response to the application of a force generally perpendicular to each of the opposing jaw members 202, 204, the respective jaw members 202, 204 are operative to grasp and clamp onto living tissue 208. Further, a single high frequency (HF) electric power source 206 is operatively connected across electrode members formed by the respective jaw members 202, 204, thereby periodically charging the respective electrode members to different electrical potentials. As a result, bipolar energy is transferred through the living tissue 208, allowing a surgeon to effect hemostatis and/or tissue-cutting actions at least in part by controlling the intensity, frequency, and/or duration of the bipolar energy applied between the respective electrode members and through the tissue 208.

As further shown in FIG. 2a, the transfer of bipolar energy through the living tissue 208 initially causes an electrical current 210 to flow through the tissue 208 generally perpendicular to contact surfaces 222, 224 of the opposing jaw members 202, 204, respectively. The flow of electrical current 210 causes the living tissue 208 to coagulate, which, in turn, causes the impedance of the tissue 208 to rise in the region between the contact surfaces 222, 224. Because uncoagulated tissue in the region generally between the periphery of the respective contact surfaces 222, 224 has a lower impedance compared to the coagulated tissue, the uncoagulated tissue provides a more favorable path for the electrical current 210 to continue flowing through the tissue 208. FIG. 2b depicts the electrical current 210 flowing through the uncoagulated tissue between the periphery of the contact surfaces 222, 224, causing what is referred to herein as a "thermal margin" (corresponding to reference numeral 212) to spread laterally and extend into the living tissue 208 in the direction of increasing coagulation. FIG. 2c depicts the thermal margin 212 spreading laterally and extending further into the living tissue 208 beyond the region between the respective jaw members 202, 204, as the electrical current 210 continues to flow through the tissue 208.

The conventional electrosurgical forceps 200 depicted in FIGS. 2a-2c have drawbacks in that the lateral thermal margin 212 can cause the impedance of the living tissue 208 near or touching the contact surfaces 222, 224 of the opposing jaw members 202, 204, respectively, to increase to a level where the flow of electrical current 210 through the tissue 208 is significantly reduced, possibly preventing further coagulation of the tissue 208. Moreover, as the thermal margin 212 spreads laterally and extends into the living tissue 208, tissue structures adjacent the region between the opposing jaw members 202, 204 may potentially become damaged, thereby limiting the overall utility of the conventional electrosurgical forceps 200. In addition, because the single HF electric power source 206 periodically charges the electrodes formed by the respective jaw members 202, 204 to different electrical potentials, an electrical short circuit can result if the contact surfaces 222, 224 of the respective jaw members 202, 204 touch one another during use. This can sometimes occur if the opposing jaw members 202, 204 are used to grasp very thin tissue, or clamp onto the living tissue 208 with excessive force. Such electrical shorting of the opposing contact surfaces 222, 224 can stop any electrical current from flowing through the living tissue 208, possibly preventing the conventional electrosurgical forceps 200 from providing hemostatis at a time when it may be most needed.

FIG. 3a depicts an illustrative embodiment of exemplary electrosurgical forceps 300 configured in accordance with the present application. As shown in FIG. 3a, the electrosurgical forceps 300 include a housing 327, a handle assembly including a fixed handle 330 and a movable handle 332, a trigger 334 for activating tissue-cutting action, a shaft 322, and an electrode assembly 301. As shown in FIG. 3a, the electrosurgical forceps 300 include a pair of opposing jaw members 302, 304 configured to form the electrode assembly 301, which can be mechanically engaged in a conventional manner at a distal end 324 of the shaft 322. A proximal end 326 of the shaft 322 is configured to mechanically engage the housing 327. The electrosurgical forceps 300 further include a rotatable assembly 340 for providing, for example, at least 330° rotation of the electrode assembly 301, a button 338 for activating tissue-coagulating action, and an electrical cable 328. The electrical cable 328 is connectable to two isolated electric power outputs, and configured to provide multiple electrical paths through the fixed handle 330, the housing 327, and the shaft 322, ultimately providing the multiple isolated electric power outputs to the electrode assembly 301.

FIG. 3b depicts a perspective view of the electrode assembly 301, including the pair of opposing jaw members 302, 304. As shown in FIG. 3b, each of the opposing jaw members 302, 304 forms two elongated electrode members within the electrode assembly 301, which is referred to herein as a quadripolar electrode assembly. Specifically, the jaw member 302 is configured to form two elongated electrode members 302.1, 302.2, and the jaw member 304 is likewise configured to form two elongated electrode members 304.1, 304.2. The elongated electrode members 302.1, 302.2, as well as the elongated electrode members 304.1, 304.2, can be mechanically isolated from one another by bonding a non-conductive epoxy bridge 316.1 between distal ends of the respective electrode members 302.1, 302.2, and bonding a non-conductive epoxy bridge 316.2 between distal ends of the respective electrode members 304.1, 304.2, or by any other suitable technique. In some embodiments, one or both of the non-conductive epoxy bridges 316.1, 316.2 may be omitted. The fixed handle 330, the movable handle 332, the housing 327, the shaft 322, and the quadripolar electrode assembly 301 mutually cooperate to move the opposing jaw members 302, 304 from an open position (as illustrated in FIG. 3a) to a closed position (as illustrated in FIG. 3b), and vice versa, as required for grasping living tissue 308 therebetween.

FIGS. 4a-4c are schematic diagrams illustrating the operation of the electrosurgical forceps 300 (see FIGS. 3a and 3b). Specifically, FIGS. 4a-4c depict electrosurgical forceps 400 that include a pair of opposing jaw members 402, 404, which schematically represent the pair of opposing jaw members 302, 304, respectively, included in the electrosurgical forceps 300. The pair of opposing jaw members 402, 404 are configured to grasp and clamp onto living tissue 408. As shown in FIGS. 4a-4c, each of the opposing jaw members 402, 404 forms two electrode members. Specifically, the jaw member 402 is configured to form two electrode members 402.1, 402.2, and the jaw member 404 is likewise configured to form two electrode members 404.1, 404.2. The electrode members 402.1, 402.2, 404.1, 404.2 are configured and arranged such that the electrode members 402.1, 404.2 are disposed directly opposite one another, the electrode members 402.2, 404.1 are disposed directly opposite one another, the electrode members 402.2, 404.2 are disposed diagonally opposite one another, and the electrode members 402.1, 404.1 are disposed diagonally opposite one another. Moreover, a first high frequency (HF) electric power source 406.1 is connected across the diagonally opposing electrode members 402.1, 404.1, and a second HF electric power source 406.2 is connected across the diagonally opposing electrode members 402.2, 404.2, electrically isolating the electrode members 402.1, 404.1 from the electrode members 402.2, 404.2.

In an exemplary mode of operation, the electrosurgical forceps 400 are operative to move the pair of opposing jaw members 402, 404 from the open position (as illustrated in FIG. 3a) to the closed position (as illustrated in FIG. 3b), and vice versa, as required for grasping the living tissue 408 therebetween. The HF electric power source 406.1 connected across the electrode members 402.1, 404.1 can be selectively activated by a user to direct bipolar energy diagonally through the living tissue 408 between the diagonally opposing first electrode members 402.1, 404.1. Likewise, the HF electric power source 406.2 connected across the electrode members 402.2, 404.2 can be selectively activated by the user to direct bipolar energy diagonally through the living tissue 408 between the diagonally opposing electrode members 402.2, 404.2. Because the electrode members 402.1, 404.1 are electrically isolated from the electrode members 402.2, 404.2, the bipolar energy generated by the HF electric power sources 406.1, 406.2 causes two separate and isolated electrical currents to flow through the living tissue 408, namely, a first electrical current 410.1 flowing through the tissue 408 between the diagonally opposing electrode members 402.1, 404.1, and a second electrical current 410.2 flowing through the tissue 408 between the diagonally opposing electrode members 402.2, 404.2. It is noted that the arrangement of the electrode members 402.1, 402.2, 404.1, 404.2 prohibits electrical current from flowing between the electrode members 402.1, 402.2 within the jaw member 402, between the electrode members 404.1, 404.2 within the jaw member 404, between the electrode members 402.1, 404.2 disposed directly opposite one another, and between the electrode members 402.2, 404.1 disposed directly opposite one another.

As shown in FIG. 4a, the transfer of bipolar energy through the living tissue 408 causes the electrical current 410.1 to flow diagonally through the tissue 408 between contact surfaces 422.1, 424.1 of the diagonally opposing electrode members 402.1, 404.1, respectively. Likewise, the transfer of bipolar energy through the living tissue 408 causes the electrical current 410.2 to flow diagonally through the tissue 408 between contact surfaces 422.2, 424.2 of the diagonally opposing electrode members 402.2, 404.2, respectively. The flow of the two separate and isolated electrical currents 410.1, 410.2 causes the living tissue 408 to coagulate, which, in turn, causes the impedance of the tissue 408 to rise in the region between the contact surfaces 422.1, 422.2 and the contact surfaces 424.1, 424.2. Because the arrangement of the electrode members 402.1, 402.2, 404.1, 404.2 prohibits electrical current from flowing between the electrode members 402.1, 404.2 disposed directly opposite one another, as well as between the electrode members 402.2, 404.1 disposed directly opposite one another, a thermal margin 412 spreads through the tissue 408 generally perpendicular to the contact surfaces 422.1, 422.2, and the contact surfaces 424.1, 424.2, in the direction of increasing coagulation, as depicted in FIG. 4*b*.

FIG. 4*c* depicts the thermal margin 412 spreading further through the living tissue 408 in the direction of increasing coagulation, as well as laterally through the living tissue 408, as the electrical currents 410.1, 410.2 continue to flow diagonally through the tissue 208. However, because electrical current is prohibited from flowing between the electrode members 402.1, 404.2 disposed directly opposite one another, and between the electrode members 402.2, 404.1 disposed directly opposite one another, the lateral thermal margin 412 is reduced, and is substantially prevented from extending into the living tissue 408 beyond the region between the opposing jaw members 402, 404. Moreover, because electrical current is also prohibited from flowing between the electrode members 402.1, 402.2 within the jaw member 402, and between the electrode members 404.1, 404.2 within the jaw member 404, unwanted desiccation of surface areas of the living tissue 408 is substantially eliminated.

In addition, because the electrode members 402.1, 404.1 are electrically isolated from the electrode members 402.2, 404.2, the risk of an electrical short circuit resulting from the directly opposing contact surfaces 422.1, 424.2 inadvertently touching one another during use, or from the directly opposing contact surfaces 422.2, 424.1 inadvertently touching one another during use, is substantially eliminated. As a result, the need to provide one or more insulating structures between the opposing contact surfaces 422.1, 424.2, and/or between the opposing contact surfaces 422.2, 424.1, to prevent such inadvertent touching of the opposing contact surfaces, is avoided, thereby facilitating low-cost manufacture of the electrosurgical forceps 400.

Figure 5B:
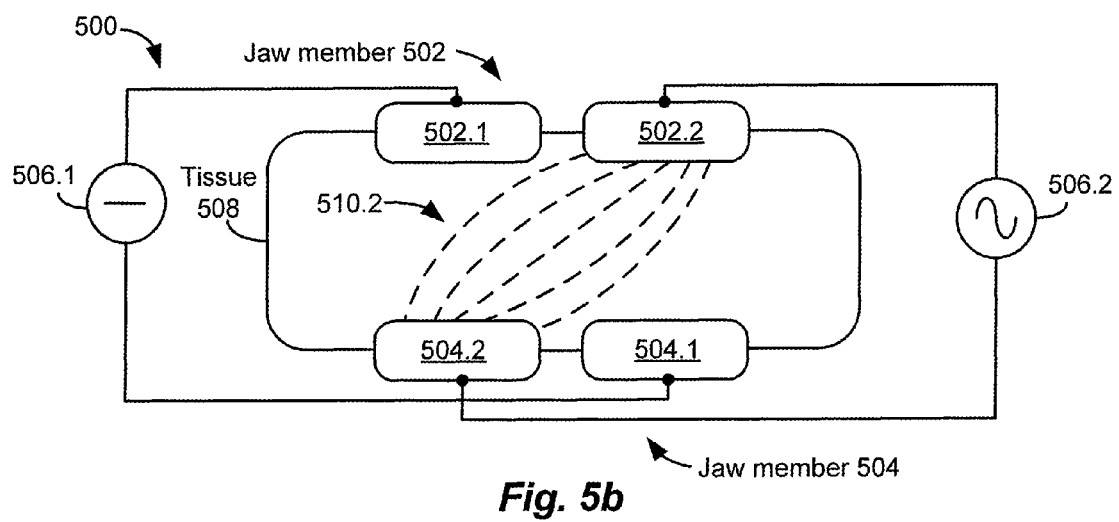

Having described the above exemplary embodiments of the disclosed electrosurgical forceps, other alternative embodiments or variations may be made. For example, FIGS. 5*a* and 5*b* are schematic diagrams further illustrating the operation of the electrosurgical forceps 300 (see FIGS. 3*a* and 3*b*). Specifically, FIGS. 5*a* and 5*b* depict electrosurgical forceps 500 that include a pair of opposing jaw members 502, 504, which schematically represent the pair of opposing jaw members 302, 304, respectively, included in the electrosurgical forceps 300. The pair of opposing jaw members 502, 504 are configured to grasp and clamp onto living tissue 508. As shown in FIGS. 5*a* and 5*b*, the jaw member 502 is configured to form two electrode members 502.1, 502.2, and the jaw member 504 is likewise configured to form two electrode members 504.1, 504.2. The electrode members 502.1, 502.2, 504.1, 504.2 are configured and arranged such that the electrode members 502.1, 504.2 are disposed directly opposite one another, the electrode members 502.2, 504.1 are disposed directly opposite one another, the electrode members 502.2, 504.2 are disposed diagonally opposite one another, and the electrode members 502.1, 504.1 are disposed diagonally opposite one another. Moreover, a first high frequency (HF) electric power source 506.1 is connected across the diagonally opposing electrode members 502.1, 504.1, and a second HF electric power source 506.2 is connected across the diagonally opposing electrode members 502.2, 504.2, electrically isolating the electrode members 502.1, 504.1 from the electrode members 502.2, 504.2.

In an exemplary mode of operation, the HF electric power source 506.1 connected across the electrode members 502.1, 504.1 can be selectively activated by a user to direct bipolar energy diagonally through the living tissue 508 between the diagonally opposing electrode members 502.1, 504.1, while the HF electric power source 506.2 connected across the electrode members 502.2, 504.2 is selectively deactivated by the user. The bipolar energy generated by the HF electric power source 506.1 causes a single electrical current 510.1 to flow through the living tissue 508 between the diagonally opposing electrode members 502.1, 504.1, as shown in FIG. 5*a*. Alternatively, the HF electric power source 506.2 connected across the electrode members 502.2, 504.2 can be selectively activated by the user to direct bipolar energy diagonally through the living tissue 508 between the diagonally opposing electrode members 502.2, 504.2, while the HF electric power source 506.1 connected across the electrode members 502.1, 504.1 is selectively deactivated by the user. The bipolar energy generated by the HF electric power source 506.2 causes a single electrical current 510.2 to flow through the living tissue 508 between the diagonally opposing electrode members 502.2, 504.2, as shown in FIG. 5*b*. Such selective activation of the HF electric power sources 506.1, 506.2, at the same time or at different times, can provide the user of the electrosurgical forceps 500 with increased flexibility while performing hemostatis and/or tissue-cutting actions during surgical procedures.

Figure 6:
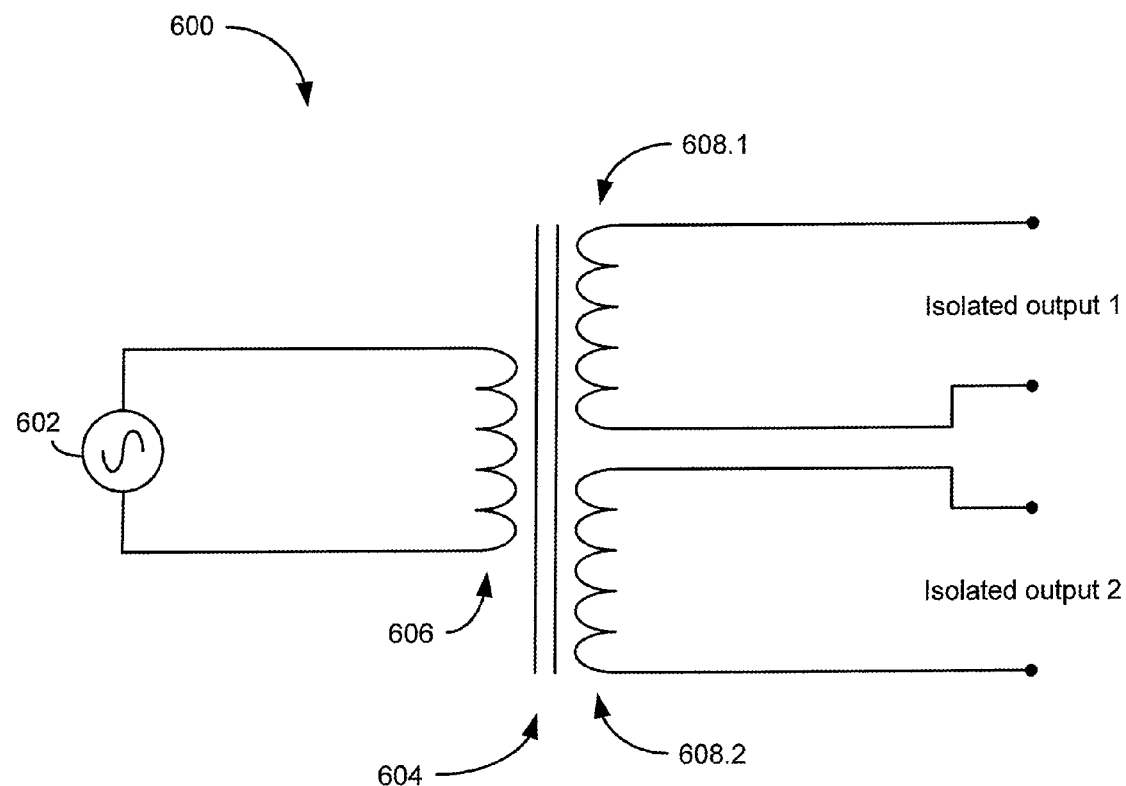
FIG. 6 is a schematic diagram of an exemplary electrical circuit for generating two isolated electric power outputs from a single high frequency (HF) electric power source, for use with the quadripolar electrode assembly of FIG. 3b.

In some embodiments, the disclosed electrosurgical forceps can be used in conjunction with a single high frequency (HF) electric power source. FIG. 6 depicts an exemplary electrical circuit 600 for generating two isolated electric power outputs, namely, an isolated output 1 and an isolated output 2, from a single HF electric power source 602. As shown in FIG. 6, the electrical circuit 600 includes the HF electric power source 602 and a transformer 604. The transformer 604 includes a single primary coil 606 operatively connected to the HF electric power source 602, a first secondary coil 608.1 for providing the isolated output 1, and a second secondary coil 608.2 for providing the isolated output 2. For example, with reference to FIGS. 4*a*-4*c*, an isolated output 1 of either polarity, provided by the secondary coil 608.1, can be operatively connected across the electrode members 402.1, 404.1 of the jaw members 402, 404, respectively. Likewise, an isolated output 2 of either polarity, provided by the secondary coil 608.2, can be operatively connected across the electrode members 402.2, 404.2 of the jaw members 402, 404, respectively. In this way, the disclosed operation of the electrosurgical forceps 400 can be achieved in a system configuration that includes a single HF electric power source.

In addition, it was described herein, with reference to FIG. 3*b*, that the quadripolar electrode assembly 301 could include the pair of opposing jaw members 302, 304, in which each of the opposing jaw members 302, 304 forms two electrode members within the quadripolar electrode assembly 301. In some embodiments, such electrode members within the quadripolar electrode assembly 301 may be toothed or non-toothed. Moreover, in some embodiments, such electrode members may be provided in each such jaw member in quantities of two or more, and in any other suitable size and/or geometry.

Figure 7:
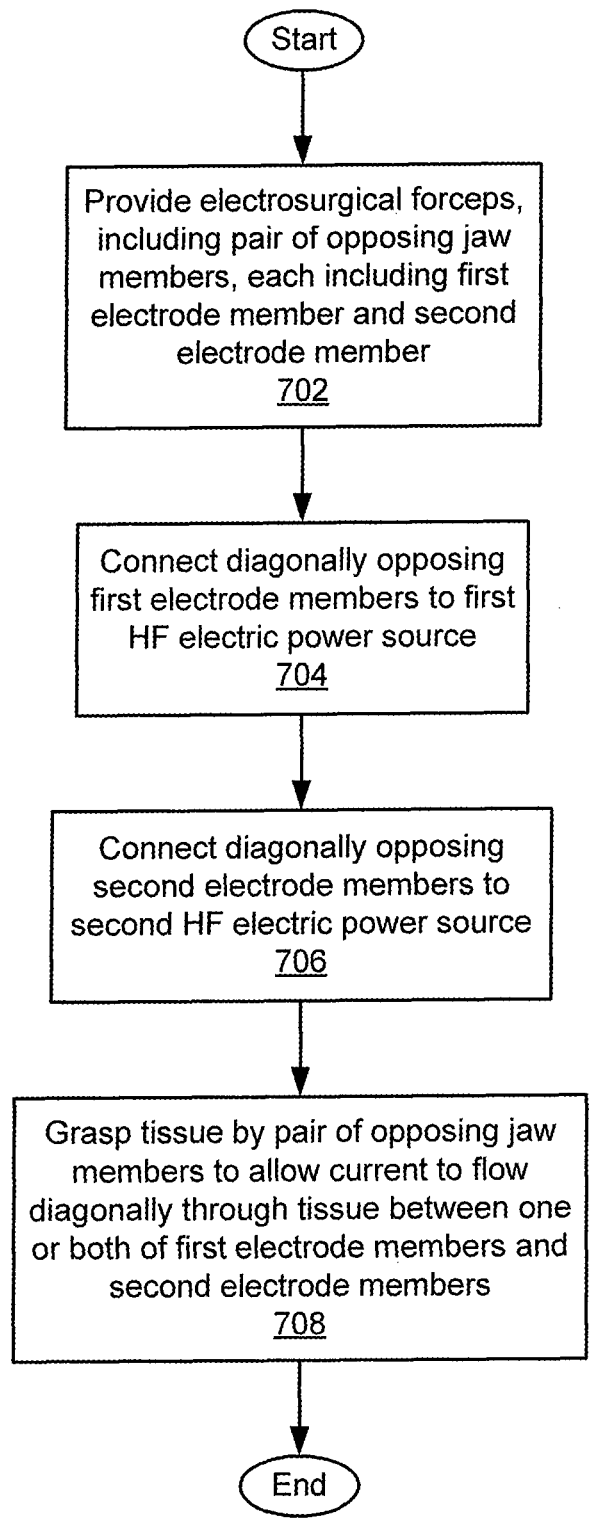
FIG. 7 is a flow diagram of a method of operating the electrosurgical forceps of FIG. 3a, incorporating the quadripolar electrode assembly of FIG. 3b.

A method of operating the disclosed electrosurgical forceps is described herein with reference to FIG. 7. As illustrated in block 702, electrosurgical forceps are provided, including a pair of opposing first and second jaw members, in which each jaw member includes a first electrode member and a second electrode member. The first and second electrode members included in the first and second jaw members, respectively, are disposed directly opposite one another, the second and first electrode members included in the first and second jaw members, respectively, are disposed directly opposite one another, the first electrode members included in the respective jaw members are disposed diagonally opposite one another, and the second electrode members included in the respective jaw members are disposed diagonally opposite one another. As illustrated in block 704, the diagonally opposing first electrode members included in the respective jaw members are operatively connected to a first high frequency (HF) electric power source. As illustrated in block 706, the second electrode members included in the respective jaw members are operatively connected to a second HF electric power source, such that the first electrode members and the second electrode members are electrically isolated from one another. As illustrated in block 708, tissue is grasped by the pair of opposing first and second jaw members to allow current to flow diagonally through the tissue between one or both of the first electrode members and the second electrode members.

It will be appreciated by those skilled in the art that modifications to and variations of the above-described systems and methods may be made without departing from the inventive concepts disclosed herein. Accordingly, the invention should not be viewed as limited except as by the scope and spirit of the appended claims.

What is claimed is:

1. A method of operating electrosurgical forceps, comprising the steps of:
providing electrosurgical forceps including a pair of opposing first and second jaw members, each jaw member including at least a first elongated straight electrode member and a second elongated straight electrode member, wherein the first and second elongated straight electrode members included in the first and second jaw members, respectively, are disposed directly opposite one another, wherein the second and first elongated straight electrode members included in the first and second jaw members, respectively, are disposed directly opposite one another, wherein the first elongated straight electrode members included in the respective jaw members are disposed diagonally opposite one another, wherein the second elongated straight electrode members included in the respective jaw members are disposed diagonally opposite one another, wherein the first elongated straight electrode member included in each jaw member has a proximal end and a distal end, and wherein the second elongated straight electrode member included in each jaw member has a proximal end and a distal end;
connecting a first non-conductive bridge member between the distal ends of the first and second elongated straight electrode members included in the first jaw member;
operatively connecting the proximal ends of the first elongated straight electrode members included in the respective jaw members to a first high frequency electric power source;
operatively connecting the proximal ends of the second elongated straight electrode members included in the respective jaw members to a second high frequency electric power source, the first elongated straight electrode members being electrically isolated from the second elongated straight electrode members; and
grasping tissue by the pair of opposing first and second jaw members to allow current to flow diagonally through the tissue between one or both of the first elongated straight electrode members and the second elongated straight electrode members.

2. The method of claim 1 further comprising:
connecting a second non-conductive bridge member between the distal ends of the first and second elongated straight electrode members included in the second jaw member.

3. The method of claim 1 further comprising:
selectively activating the first high frequency electric power source; and
selectively activating the second high frequency electric power source,
thereby allowing a first current to flow diagonally through the tissue between the first elongated straight electrode members, and a second current to flow diagonally through the tissue between the second elongated straight electrode members.

4. The method of claim 1 further comprising:
selectively activating the first high frequency electric power source; and
selectively deactivating the second high frequency electric power source,
thereby allowing current to flow diagonally through the tissue between the first elongated straight electrode members, and prohibiting current from flowing diagonally through the tissue between the second elongated straight electrode members.

5. The method of claim 4 further comprising:
selectively activating the second high frequency electric power source; and
selectively deactivating the first high frequency electric power source,
thereby allowing current to flow diagonally through the tissue between the second elongated straight electrode members, and prohibiting current from flowing diagonally through the tissue between the first elongated straight electrode members.

6. Electrosurgical forceps, comprising:
a pair of opposing first and second jaw members operative to grasp tissue therebetween, each jaw member including at least a first elongated straight electrode member and a second elongated straight electrode member,
wherein the first and second elongated straight electrode members included in the first and second jaw members, respectively, are disposed directly opposite one another, and the second and first elongated straight electrode members included in the first and second jaw members, respectively, are disposed directly opposite one another,
wherein the first elongated straight electrode members included in the respective jaw members are disposed diagonally opposite one another, and the second elongated straight electrode members included in the respective jaw members are disposed diagonally opposite one another, and
wherein the first elongated straight electrode member included in each jaw member has a proximal end and a distal end, and the second elongated straight electrode member included in each jaw member has a proximal end and a distal end; and
a first non-conductive bridge member connected between the distal ends of the first and second elongated straight electrode members included in the first jaw member,
wherein the proximal ends of the first elongated straight electrode members included in the respective jaw members are operatively connectable to a first high frequency electric power source, and the proximal ends of the second elongated straight electrode members included in the respective jaw members are operatively connectable to a second high frequency electric power source, the first elongated straight electrode members being electrically isolated from the second elongated straight electrode members, thereby allowing current to flow diagonally through the tissue between one or both of the first elongated straight electrode members and the second elongated straight electrode members.

7. The electrosurgical forceps of claim 6 further comprising:

a second non-conductive bridge member connected between the distal ends of the first and second elongated straight electrode members included in the second jaw member.

8. A system, comprising:

electrosurgical forceps including a pair of opposing first and second jaw members operative to grasp tissue therebetween, each jaw member including at least a first elongated straight electrode member and a second elongated straight electrode member, wherein the first and second elongated straight electrode members included in the first and second jaw members, respectively, are disposed directly opposite one another, and the second and first elongated straight electrode members included in the first and second jaw members, respectively, are disposed directly opposite one another, wherein the first elongated straight electrode members included in the respective jaw members are disposed diagonally opposite one another, and the second elongated straight electrode members included in the respective jaw members are disposed diagonally opposite one another, and wherein the first elongated straight electrode member included in each jaw member has a proximal end and a distal end, and the second elongated straight electrode member included in each jaw member has a proximal end and a distal end;

a first non-conductive bridge member connected between the distal ends of the first and second elongated straight electrode members included in the first jaw member;

a first high frequency electric power source connected to the proximal ends of the first elongated straight electrode members included in the respective jaw members, the first high frequency electric power source being operative to generate a first isolated electric power output across the first elongated straight electrode members included in the respective jaw members; and a second high frequency electric power source connected to the proximal ends of the second elongated straight electrode members included in the respective jaw members, the second high frequency electric power source being operative to generate a second isolated electric power output across the second elongated straight electrode members included in the respective jaw members, thereby allowing current to flow diagonally through the tissue between one or both of the first elongated straight electrode members and the second elongated straight electrode members.

9. The system of claim 8 further comprising:

a second non-conductive bridge member connected between the distal ends of the first and second elongated straight electrode members included in the second jaw member.

\* \* \* \* \*